United States Patent
Piers et al.

(10) Patent No.: US 7,677,725 B2
(45) Date of Patent: Mar. 16, 2010

(54) OPHTHALMIC LENSES CAPABLE OF REDUCING CHROMATIC ABERRATION

(75) Inventors: Patricia Piers, Groningen (NL); Henk Weeber, Groningen (NL)

(73) Assignee: AMO Groningen B.V., Groningen (NL)

( * ) Notice: Subject to any disclaimer, the term of this patent is extended or adjusted under 35 U.S.C. 154(b) by 1318 days.

(21) Appl. No.: 11/099,342

(22) Filed: Apr. 5, 2005

(65) Prior Publication Data
US 2007/0002444 A1    Jan. 4, 2007

Related U.S. Application Data

(60) Provisional application No. 60/559,472, filed on Apr. 5, 2004.

(51) Int. Cl.
*G02C 7/02* (2006.01)

(52) U.S. Cl. .................. 351/177; 351/159; 351/175; 623/6.31; 623/6.3

(58) Field of Classification Search .............. 351/177
See application file for complete search history.

(56) References Cited

U.S. PATENT DOCUMENTS

| 5,050,981 | A | 9/1991 | Roffman |
| 5,117,306 | A | 5/1992 | Cohen |
| 5,895,422 | A | 4/1999 | Hauber |
| 6,082,856 | A | 7/2000 | Dunn et al. |
| 6,338,559 | B1 | 1/2002 | Williams et al. |
| 2003/0063254 | A1 | 4/2003 | Piers et al. |
| 2003/0169491 | A1* | 9/2003 | Bender et al. ............... 359/356 |
| 2004/0169820 | A1* | 9/2004 | Dai et al. ..................... 351/246 |
| 2005/0099589 | A1* | 5/2005 | Ishak ........................... 351/44 |

FOREIGN PATENT DOCUMENTS

| WO | WO 0189424 | 11/2001 |
| WO | WO 02084381 | 10/2002 |

OTHER PUBLICATIONS

Allen L. Cohen, "Practical design of a bifocal hologram contact lens or intraocular lens", *Applied Optics*, vol. 31, No. 19, Jul. 1, 1992, pp. 3750-3754.
L.N. Thibos et al, "Theory and measurement of ocular chromatic aberration", *Vision Res.*, vol. 30, No. 1, 1990, pp. 33-49.
Susana Marcos et al, "A new approach to the study of ocular chromatic aberrations", *Vision Research*, 39 (1999), pp. 4309-4323.
Larry N. Thibos et al, "The chromatic eye: a new reduced-eye model of ocular chromatic aberration in humans", *Applied Optics*, vol. 31, No. 19, Jul. 1, 1992, pp. 3594-3600.

(Continued)

*Primary Examiner*—Jessica T Stultz

(57) ABSTRACT

A method of designing an aspheric ophthalmic lens with both refractive and diffractive powers that is capable of reducing chromatic aberration and at least one monochromatic aberration of an eye comprises combining aspherical refractive and diffractive surfaces, selecting an appropriate eye model, establishing a design lens having at least one aspheric surface with a capacity to reduce monochromatic aberration in said eye model, establishing a diffractive lens element that corrects for chromatic aberration of the model eye; and adjusting the lens surface design in order to obtain a suitably high polychromatic image quality in a form that is weighted to comply with a spectral merit function.

18 Claims, 9 Drawing Sheets

OTHER PUBLICATIONS

John A. Mordi et al, "Influence of Age of Chromatic Aberration of the Human Eye", *American Journal of Optometry & Physiological Optics*, vol. 62, No. 12, 1985, pp. 864-869.

Jo Ann Smith Kinney, "Sensitivity of the Eye to Spectral Radiation at Scotopic and Mesopic Intensity Levels", *Journal of the Optical Society of America*, vol. 45, No. 7, Jul. 1955, pp. 507-514.

S. Kokoschka et al, "Influence of Field Size on the Spectral Sensitivity of the Eye in the Photopic and Mesopic Range", *American Journal of Optometry & Physiological Optics*, vol. 62, No. 2, 1985, pp. 199-126.

William O. Dwyer et al, "Racial Differences In Color Vision: Do They Exist?", *American Journal of Optometry & Physiological Optics*, vol. 52, Mar. 1975, pp. 224-229.

Sarah L. Alvarez et al, "Spectral threshold: measurement and clinical applications", *British Journal of Ophthalmology*, 1983, 67, pp. 504-507.

F.S. Said et al, "The Variation with Age of the Spectral Transmissivity of the Living Human Crystalline Lens", *Gerontologia*, 1959, pp. 213-231.

Antonio Guirao et al, "Corneal wave aberration from videokeratography: accuracy and limitations of the procedure", *Journal of Optical Sociery of Arnerica,* vol. 17, No. 6, Jun. 2000, pp. 955-965.

R. Navarro et al, "Accommodation-dependent model of the human eye with aspherics", *Journal of Optical Society of America*, vol. 2, No. 8, Aug. 1985, pp. 1273-1281.

Guy Verriest, "The Spectral Curve of Relative Luminous Efficiency in Different Age Groups of Aphakic Eyes", *Pathology*, Mod. Probl. Ophthal., vol. 13, 1974, pp. 314-317.

M. Scott Griswold et al, "Scotopic Spectral Sensitivity of Phakic and Aphakic Observers Extending into the Near Ultraviolet", *Vision res.*, vol. 32, No. 9, 1992, pp. 1739-1743.

Geun-Young Yoon et al "Visual Performance after correcting the monochromatic and chromatic aberrations of the eye" J. Opt. Soc. Am A/vol. 19 No. 2/ Feb. 2002.

* cited by examiner

OPHTHALMIC LENSES CAPABLE OF REDUCING CHROMATIC ABERRATION

RELATED APPLICATION

This application claims priority under 35 U.S.C. §119 of U.S. Application Ser. No. 60/559,472 filed Apr. 5, 2004.

BACKGROUND OF INVENTION

A wavefront passing the eye will be influenced by the optical parts of the eye such that for example chromatic aberration is provided to the wavefront. The reason is that the refractive indices of the materials in the optical parts of the eye differ for different wavelengths. Thus light having different wavelengths will be refracted a different amount and they will fall on the retina at different places, i.e. different colors can not be focused to the same point. This is called chromatic aberration.

Recently there has been much interest in the correction of the monochromatic aberrations of the eye. It has been revealed that when all monochromatic aberrations are corrected in the human visual system, it serves to unmask the chromatic aberration of the eye, see Yoon G. and Williams D. R.: "Visual performance after correcting the monochromatic and chromatic aberrations of the eye". J. Opt. Soc. Am. A, 19, 266-275 (2002). Therefore, in order to optimize the optical quality of the eye, a combination of monochromatic and chromatic aberrations needs to be corrected. A diffractive pattern could be configured to provide a passing wavefront with chromatic aberration of the opposite sign as chromatic aberration from the eye. Thus a diffractive pattern can be used to correct for chromatic aberration introduced to a wavefront from the optical parts of the eye.

Some background theory of chromatic aberration can be found in, for example Chapter 17 in "Optics of the Human Eye" written by David A. Atchison and George Smith. A theoretical background of the diffractive pattern could be found in the article "Practical design of a bifocal hologram contact lens or intraocular lens", Allen L. Cohen, Applied Optics 31(19)(1992).

Ophthalmic lenses, which on at least one surface comprises a diffractive pattern for correcting for chromatic aberration are known from for example U.S. Pat. Nos. 5,895,422, 5,117, 306 and 5,895,422. These lenses do, however not, compensate for other aberrations provided by the eye surfaces. WO 01/89424 teaches methods how to design aspheric lenses that compensate for spherical aberration. However, with some applications these lenses will provide the eye with an increase in chromatic aberration. It is therefore a need of an ophthalmic lens for correcting refractive errors that also can correct for monochromatic and chromatic aberrations.

The chromatic aberration of the eye could be measured by using vernier methods such as those similar to the methods outlined in Thibos et. al., "Theory and measurement of ocular chromatic aberration", Vision Res., 30, 33-49 (1990) and Marcos et. al, Vision Research, 39, 4309-4323, (1999). Alternative ways for measuring chromatic aberration are described in a textbook, "Optics of the Human Eye" by David A. Atchison and George Smith, published by Butterworth-Heinemann, ISBN 0-7506-3775-7.

The longitudinal chromatic aberration of the eye is very well understood and has been shown to have very similar values from subject to subject (Thibos et. al., "The chromatic eye: a new reduced eye model of ocular chromatic aberration in humans", Applied Optic, 31, 3594-3600, (1992)). It has also been shown to be stable with age (Mordi et. al., "Influence of age on chromatic aberration of the human eye", Amer. J. Optom. Physiol. Opt., 62, 864-869 (1985)). Hereby an ophthalmic lens to correct for the average chromatic aberration of the eye could be designed.

WO 02/084381 describes a method of how design a hybrid refractive/diffractive ophthalmic lens, wherein chromatic aberration will be reduced by means of the diffractive element, while spherical aberration will be reduced through the use of an aspheric element. Also U.S. Pat. No. 6,338,559 suggests lenses that reduce monochromatic and chromatic aberrations principally by using an apodization filter. Although these efforts are significant, there are still needs to further improve chromatic aberration reduction and the visual quality while adapting the lenses further optimized to meet the needs of the human eye. The present invention aims at meeting such requirements with a hybrid type lens.

DESCRIPTION OF THE INVENTION

It is the principal object of the present invention to provide ophthalmic lenses of the type having both a refractive and a diffractive power that can correct for at least one higher order monochromatic aberration with improved visual quality and improved capacity to reduce for chromatic aberration, by optimizing the refractive and diffractive lens elements using a spectral merit function and/or using a spectral filter.

In the following sections, including the appended claims, a number of terms are used which hereby are given definitions.

The term "aspheric" will refer to rotationally symmetric, asymmetric and/or irregular surfaces, i.e. all surfaces differing from a sphere.

The term "monochromatic aberration" refers to optical aberrations represented by third and higher order radial Zernike polynomials (excluding piston, tip and tilt), or equivalent aberrations, as described by other metrics as understood by those skilled in the art. Reference is given to WO 01/89424 wherein the significance of aberration terms is described in more detail. The monochromatic aberration could be for example astigmatism, coma, spherical aberration, trifoil, tetrafoil or higher aberration terms.

"Chromatic aberration" is defined conventionally as that term is understood by a person skilled in the art, but preferably and substantially refers to axial or longitudinal chromatic aberration. This term and the possibility to reduce chromatic aberration with a diffractive lens element with diffractive wavelength dependent power is explained in more detail in WO 02/084381, which hereby is incorporated as a reference.

"A model eye" is an optical representation used to reproduce physiological properties of the eye. It typically includes all of or selected elements of the eye such as the cornea, aqueous humor, the lens and the vitreous. It may use aspheric or spherical components. It may be a monochromatic or polychromatic description. These factors are defined depending on which properties it is intended to reproduce. The skilled person is aware of several different such models including the eye model described by Navarro (1985). The eye model could also be based on measurements taken on an individual eye of an individual patient or a selected group of eyes. The skilled person understands that the exact parameters of the lens designed in accordance with the present invention will depend on the selected eye model.

"A spectral merit function" is a wavelength dependent function used to decrease the defects in a lens design, which diminish polychromatic optical quality. It is an arbitrary function, which provides weight factors corresponding to wavelengths of light in the visual range. This function is employed by calculating a monochromatic metric of visual quality for discrete wavelengths and weighting these monochromatic metrics with discrete values of the wavelength dependent spectral merit function. When these weighted values are summed (the use of the sum of the squares is also possible) a single value is obtained which indicates to the designer the polychromatic optical quality of a given lens design. This is defined as the polychromatic image quality. Metrics of optical quality of the eye include but are not limited to the following:

a) Polychromatic or monochromatic aberration—when aberration is decreased the optical quality of the eye improves. The quantity of aberration can be described by indicating the amount of an individual aberration such as spherical aberration, coma, or astigmatism or by indicating the root mean square wavefront aberration.

b) Spread functions—spread functions describe the form of the image formed on the retina. Examples of spread functions include the point spread function and the line spread function. Measurements derived from these functions, such as the Strehl ratio, may also be used as metric of optical quality.

c) Transfer functions—transfer functions describe the relative contrast of the image formed on the retina. The optical transfer function or its components, the modulation and phase transfer function, may also be used as metrics of optical quality.

As stated above, these metrics for optical quality indicate imperfections in the image formed on the retina. As a result they cause a subject's visual quality to be diminished, as such we refer to each of these metrics as "a metric of visual quality". Other metrics of visual quality consist of direct measurements of visual performance including, but not limited to, acuity techniques and contrast sensitivity techniques.

In a first general aspect, the present invention relates to a method of designing an aspheric ophthalmic lens with both refractive and diffractive powers that is capable of reducing chromatic aberration and at least one monochromatic aberration of an eye or a model eye. Generally, the design method includes the combination of spherical and diffractive surfaces in order to find their optimal relationship and it includes the initial selection of an appropriate eye model and the establishment of an aspheric design lens with a capacity of reducing monochromatic aberration in the eye model. Further a diffractive lens element that, at least partially, corrects for chromatic aberration of the model eye is introduced, whereupon the polychromatic image quality in a form that is weighted with a spectral merit function is assessed. The polychromatic image quality is optimised by changing the lens surface. Finding the optimal surface design includes adjusting the ratio of refractive lens power to diffractive lens element power, or the asphericity of a lens surface, or adjusting the profile of the diffractive lens element, or combinations or by combining such redesigns. The spectral merit function preferably describes a wavelength dependent sensitivity of the eye for a selected lighting and/or viewing conditions. More preferably, the spectral merit function is a spectral luminosity function of the human eye. Different eye conditions for the spectral merit functions can be selected as appropriate. Accordingly spectral merit functions for the phakic, the aphakic or the pseudophakic eye may be employed. Especially preferred spectral merit functions are selected among the photopic, the scotopic and the mesopic luminosity functions. Combinations of spectral merit functions are also conceivable to use with present invention, as well as spectral merit functions derived for an individual or for elected population groups. Such groups can be selected according to different criteria, such as being eligible for cataract surgery, having certain ocular diseases or having undergone specific ocular surgical processes, such as corneal refractive surgery.

The design lens preferably has a preset total lens power having a starting refractive power and diffractive power. The method further, preferably comprises the selection of an appropriate design wavelength.

The method as generally outlined in the above section, can also comprise an estimation of the power of the model eye system including the design lens at different wavelengths and thereby an estimation of the chromatic aberration of the eye model, an estimation of an ideal correction function describing how the system can eliminate chromatic aberration and from that point can a linear correction function of wavelength depending power approximating said ideal correction function be estimated. A diffractive lens element for the design lens that has the same wavelength dependent power as the approximate linear correction function can subsequently be construed before estimating the diffractive power of the diffractive lens element and adjusting the refractive lens power so the sum of diffractive and refractive powers complies with the preset total lens power. The method further includes the determination of a polychromatic metric for the visual quality, which is obtained by calculating metrics for visual quality for a number of discrete wavelengths; each of these subsequently is weighed using the corresponding value obtained from the spectral merit function. From that point, the lens surface design is adjusted until the optimal weighted polychromatic visual quality metric is obtained. Preferably, the metrics for visual quality are monochromatic modulation transfer functions (MTFs) for discrete wavelengths each weighted by the corresponding value obtained from the spectral merit function and the polychromatic metric of visual quality is a polychromatic modulation transfer function (PMTF) construed from said MTFs, as will be explained below in greater detail. A suitable way of evaluating if a sufficiently high visual quality is obtained is to consider if the modulation at spatial frequency at 50 cycles per millimetres of the weighted PMTF approaches the theoretical limit. The ratio of refractive lens power to diffractive lens power, the asphericity of a lens surface, or the profile of the diffractive surface, or combinations thereof can then be adjusted until an acceptable image quality is obtained. Alternatively, other wavelength dependent image quality metrics such as the Strehl ratio or could also be employed in the optimisation when minimizing the longitudinal chromatic aberration (also weighted using the spectral merit function). Changing the asphericity of a lens surface, typically may be performed by changing the conical constant (cc) in the asphericity formula describing such a surface that is provided below in the detailed specification.

The spectral merit function employed with the inventive method can be selected according to various principles. This merit function may be the spectral luminosity function of the human eye or the sensitivity of the eye to different wavelengths of light. The luminosity function of the eye varies depending on the surrounding lighting conditions. In this way an ophthalmic lens will be optimized for mesopic conditions by choosing to use the mesopic luminosity function as the spectral merit function, see Kinney, J. A. (1955) "Sensitivity of the eye to spectral radiation at scotopic and mesopic intensity levels": *J Opt Soc Am* 45(7): 507-14 and Kokoschka, S. and W. K. Adrian (1985) "Influence of field size on the spectral sensitivity of the eye in the photopic and mesopic range": *Am J Optom Physiol Opt* 62(2): 119-26. Also, an ophthalmic lens could be optimized for photopic conditions by choosing to use the photopic luminosity function [CIE Technical Report (1990). CIE 1988 2° spectral luminous efficiency function for photopic vision, CIE Publ. No. 86.] as the spectral merit function or a lens could be optimized for scotopic conditions by choosing to use the scotopic luminosity function [CIE Proceedings 1951] as the spectral merit function. The luminosity function also varies with race [Dwyer, W. O. and L. Stanton (1975). "Racial differences in color vision: do they exist?" *Am J Optom Physiol Opt* 52(3): 224-9.], presence of ocular disease [Alvarez, S. L., P. E. King-Smith, et al. (1983). "Spectral threshold: measurement and clinical applications." *Br J Ophthalmol* 67(8): 504-7], presence of color vision deficiencies (protanope, deuteranope, or tritanope) [Wyszecki, G., Stiles W. S., (1982). "Color Science: Concepts and Methods, Quantitative Data and Formulae, 2nd Edition." John Wiley and Sons, New York]. All of these factors may enter into the designer's choice of the spectral merit function. The transmittance of the ocular media or the presence of spectral filters, such as the natural human lens, also affects the luminosity function of the human eye. For example the luminosity function of an aphakic subject is very different from that of a phakic subject because the natural human lens filters out certain wavelengths of light (the amount that it filters per wavelength is dependent on the age of the subject) [Said, F. S. and R. A. Weale (1959). "The variation with age of spectral tranmissivity of the living human crystalline lens." *Gerontologia* 3: 213-231.]. The spectral merit function may also be chosen to reflect these wavelength dependent parameters. The luminosity function also varies with the area of the target viewed and the viewing angle [Kokoschka, S. and W. K. Adrian (1985). "Influence of field size on the spectral sensitivity of the eye in the photopic and mesopic range." *Am J Optom Physiol Opt* 62(2): 119-26] so that a merit function could be used to design a lens for on axis (foveal) or peripheral viewing conditions. A spectral merit function could also be used to design an ophthalmic lens to be used for lighting conditions with different spectral content or for the viewing of different objects with specific spectral content. In these cases the color spectrum of the visual scene and/or the lighting conditions could be included as weighting factors in the spectral merit function. Accordingly, with the present invention, ophthalmic lenses can be designed which correct for both chromatic aberration and at least one monochromatic aberration that improves the visual quality for patients under photopic lighting conditions, scotopic lighting conditions, mesopic lighting conditions, for a colorblind patient (protanope deuteranope or tritanope), or for a patients for on axis viewing (foveal) or off axis viewing (peripheral).

In the optimization methods of the inventive lenses many design parameters need to be considered and the resulting lens may have many different configurations, while the form of the diffractive surface and/or the aspheric surface will be optimized using a spectral merit function. The MTF of an eye model containing the refractive/diffractive lens will be wavelength dependent. The wavelength dependent MTF will be weighted by the spectral merit function and the lens design will be optimized to maximize the weighted MTF. Any wavelength dependent metric of image quality may be weighted by the spectral merit function and used to optimize the lens design.

According to one preferred embodiment of the present invention, the spectral merit function is a spectral luminosity function of the human eye. The luminosity function can originate from an individual or be derived from a selected specific population, as it varies with ethnical background, with presence of ocular specific diseases, and with color vision deficiencies. More specifically, the spectral merit function is selected among photoptic luminosity function, the mesopic luminosity function and the scotopic luminosity function, or combinations of these functions.

According to one design principle of the present invention, the design wavelength coincides with the wavelength of the efficiency maximum of the spectral merit function, which in one example is set at 550 nm.

According to a specific aspect of the inventive method, the design lens is provided with a wavelength filter that eliminates, or partially eliminates a desired wavelength range. The filter can, for example, be a blue light chromophore, or be a filter, which provides light absorption equivalent to that of the natural crystalline lens at a specific age. Suitable blue light chromophores can be yellow dyes. The skilled person is aware of numerous suitable yellow days and how to incorporate them in the lens, for example by copolymerisation with the lens forming monomers. Reference is hereby given to U.S. Pat. Nos. 5,274,663; 5,528,322; 5,543,504; 5,662,707; 5,693,095; 5,919,880; 6,310,215; and 6,448,304. Besides, correcting for bifocality, as explained in the following section, the chromophores can be used to filter out wavelengths that are not focused on the retina which otherwise would contribute to undesired chromatic aberration. The inclusion of a chromophore material aids in the correction of chromatic aberration because the filtered wavelengths no longer need to be incorporated in the optimization procedure or provide for lower weighting factors in the spectral merit function and the resulting lens design will be better corrected for the remaining wavelengths or the wavelengths with higher weighting factors in the spectral merit function. Alternatively, spectral filters that filter out different wavelengths to different degrees can be employed with the present invention. For example, a spectral filter having a transmission profile similar to the natural human lens can be selected. Thereby, will at least shorter wavelengths be partially eliminated.

According to another specific aspect of the inventive method, bifocality of the lens, as introduced by the diffractive lens element can be avoided or at least partially eliminated. The efficiency of the diffractive lens fluctuates, depending on the wavelength. When a diffractive lens is used at its usual design wavelength of 550 nm (the peak sensitivity of the eye), the lens efficiency will be lower at lower and higher wavelengths, while the efficiency of higher order foci will increase for these wavelengths. The result is that at specific wavelengths, the lens will behave as a bifocal lens. Within the visible light range, this specifically will occur at lower wavelengths, where the $1^{st}$ and $2^{nd}$ order foci will have approximately equal efficiency. In order to avoid this phenomenon, it is suggested with the present invention to employ a design wavelength lower than 550 nm, thereby removing the bifocal wavelength outside the range of visible light. In one embodiment, the design wavelength is set at 500 nm, while the selected spectral merit function is a pseudophakic photoptic luminosity function (having a maximum sensitivity, or peak of the spectral merit function is 550 nm). Alternatively, to avoid multifocality of the designed lens, wavelengths for which the lens significant efficiency for higher order foci (generated from the diffractive lens element) are estimated and a spectral filter capable of eliminating, or significantly reduce the transmission of these wavelengths is included, thereby essentially eliminating the problem of multifocality. In one embodiment, the spectral filter is a blue light filter that preferably eliminates wavelengths below 420 nm.

The preset monochromatic aberration to be corrected with the lenses designed with the inventive method, preferably is spherical aberration. Suitably, the design lens has an aspheric surface made to compensate for spherical aberration from a model cornea which be construed from corneal topography of an individual patient, or be an average cornea resulting from averaged corneal topography determinations of an elected population, for example a population elected to undergo cataract surgery as explained in greater detail in the aforementioned WO 01/89424.

As also explained in WO 02/084381, the method can involve evaluating if the aberration terms signifying the aberrations of a wavefront have passing said design lens with a sufficiently chromatic aberration reducing diffractive element deviates from the preset capacity of the lens to correct for monochromatic aberration terms and optionally redesigning at least one surface of the design lens until the aberration terms sufficiently complies with said preset capacity.

The diffractive lens element can be a diffractive surface profile consisting of a number of concentric rings, wherein the profile height of the diffractive surface profile when multiplied by the difference in refractive index between the design lens and the surrounding medium equals an integer number of the design wavelength.

In one specific embodiment, the design wavelength is set to 550 nm, the Navarro eye model is selected and a pseudophakic photoptic luminosity function is used as the spectral merit function. An aspheric silicone design lens with a preset power of 20 diopters is selected. A polychromatic modulation transfer function (PMTF) for the so designed lens is obtained by calculating modulation transfer functions (MTFs) for discrete wavelengths in the visible range each weighed from compensation with a value obtained from the pseudophakic photoptic luminosity function. A design lens having a diffractive power of 4.7 diopters and a refractive power of 15.3 diopters is construed and is found to result in a suitably acceptable image quality as represented by the modulation at a spatial frequency of 50 cycles per millimetre of the PMTF. To construe modulation transfer functions and a resulting polychromatic transfer function 38 discrete wavelengths were used 10 nm steps in the visible range of 390 to 760 nm. The so designed lens is equi-biconvex with a diffractive surface pattern superimposed on the anterior aspheric surface with a first zone of the diffractive surface pattern of 0.95 mm zone width.

In another specific embodiment, the design wavelength is 550 nm, the eye model is according to Navarro and the spectral merit function consists of both the transmission function of natural human crystalline lens and an aphakic photoptic luminosity function. An aspheric silicone design lens with a preset power of 20 diopters is used with a diffractive surface profile superimposed on the aspheric surface. A polychromatic modulation transfer function (PMTF) for the so designed lens is obtained by calculating modulation transfer functions (MTFs) for discrete wavelengths in the visible range each weighed from compensation with a value obtained from the selected spectral merit function. A design lens having a diffractive power of 4.5 diopters and a refractive power of 15.5 diopters is construed and is found to result in a suitably acceptable image quality as represented by the modulation at a spatial frequency of 50 cycles per millimetre of the PMTF. To construe modulation transfer functions and a resulting polychromatic transfer function 38 discrete wavelengths were used 10 nm steps in the visible range of 390 to 760 nm. The so designed lens is equi-biconvex with a diffractive surface pattern superimposed on the anterior aspheric surface with a first zone of the diffractive surface pattern of 1.0 mm zone width.

One suitable way of employing the inventive method includes the following steps:
choosing an appropriate spectral merit function and design wavelength;
selecting an eye model with a refractive aspheric ophthalmic lens having an aspheric surface (with or without a chromophore material in the lens) of a predetermined refractive power and a predetermined amount of at least one monochromatic aberration;
estimating the power of said eye model at different wavelengths, so as to determine the chromatic aberration of said eye model;
estimating a correction function, which approximately replicates how the power would vary with wavelength in order to ideally compensate for the chromatic aberration of the eye model weighted by the spectral merit function;
finding a linear function of how power varies with the wavelength, which suitably approximates said correction function;
calculating a provisional zone width of a diffractive profile corresponding to this linear function and also calculating the diffractive power of this diffractive profile;
reducing the refractive power of the refractive ophthalmic lens by the amount of power calculated for the diffractive profile;
calculating the polychromatic MTF (weighted by the spectral merit function); evaluating the polychromatic MTF and if necessary adjusting the refractive to diffractive power until a suitably high polychromatic image quality is obtained by the resulting PMTF, while holding the ophthalmic lens total power at the predetermined value.

If necessary, to further improve the visual quality represented by the resulting PMTF, additional lens design changes may be conducted, such as changing a lens surface asphericity or modifying the diffractive surface pattern profile height, or the design of the profile steps.

The present invention also includes ophthalmic lenses designed with principles of the method, preferably the ophthalmic lenses are intraocular lenses aimed to replace a defective natural crystalline lens. The anterior surface of the lens can be an aspheric surface, on which a diffractive profile is superimposed. Alternatively, the anterior surface of the lens is an aspheric surface and the posterior surface of the lens is flat and has a diffractive profile. Also other combinations are possible. For example a diffractive profile could be provided on both the anterior and the posterior surface. Both the anterior and posterior surfaces could also be aspheric. The skilled person can readily identify alternative lens configurations. The ophthalmic lens could be configured to be a phakic or pseudophakic intraocular lens (IOL), a spectacle lens or a contact lens. In the examples described below the lenses are pseudophakic IOLs. The material used in the example lenses described below is a foldable silicone high refractive index material described in U.S. Pat. No. 5,444,106. Other materials are however also possible for these lenses. For example PMMA (Poly-methylmethacrylat), hydrogels and acrylics are suitable materials. The exemplified lenses have a power of 20D. However, the lenses could be designed to have any other suitable power. Also negative lenses are possible.

Most generally, the aspheric ophthalmic lenses according to the present invention have both a refractive and a diffractive powers and can reduce chromatic aberration and at least one monochromatic aberration, while they have the lens form adjusted as suggested above in order to obtain a suitably high polychromatic image quality in a form that is weighted with a spectral merit function, as earlier defined. The lenses may include a chromophore, which acts as a blue light filter. Suitably, the chromophore is a blue light absorbing yellow dye. The diffractive lens element preferably is a diffractive surface profile consisting of a number of concentric rings, wherein the profile height of the diffractive surface profile when multiplies by the difference in refractive index between the design lens and the surrounding medium equals an integer number of the design wavelength employed with the lens design process.

DETAILED AND EXEMPLIFYING DESCRIPTION OF THE INVENTION

The form of the diffractive surfaces profile(s) preferred in the present invention can be characterized by their so-called phase functions. This phase function describes the additional phase that is added to a ray when it passes the diffractive surface. This additional phase is dependent on the radius of the lens where the ray strikes the surface. For radially symmetric diffractive surfaces this function can be described using Equation 1.

$$\phi(r) = \frac{2\pi}{\lambda}(DF0 + DF1r + DF2r^2 + DF3r^3 + DF4r^4 + \ldots) \quad (1)$$

Where r is the radial coordinate, $\lambda$ the wavelength and DF0, DF1 etc. are the coefficients of the polynomial. Diffractive surfaces can be designed to have monofocal or multifocal properties dependent on this phase function.

To compensate for the spherical aberration, an aspherical surface, with a lateral height described by Equation 2, preferably is introduced to the refractive part of the lens. An aspheric surface can be configured to counteract the spherical aberration introduced by the optical parts of the eye and by the diffractive part of the lens. All the optical parts of the eye do not necessarily have to be considered. In one embodiment it is sufficient to measure the spherical aberration introduced by the cornea of the eye and compensate for only the spherical aberration provided by the cornea and optionally also for the spherical aberration introduced by the diffractive part of the lens. For example Zernike terms could be used to describe the optical surfaces of the eye and thus also be used to configure the aspheric surface of the lens, which is adapted to compensate for the spherical aberration. Table 1 shows the first 15 normalized Zernike terms and the aberrations each term signifies. The spherical aberration is the $11^{th}$ normalized Zernike term. The designing of a lens that is adapted to compensate for aberrations as expressed in Zernike terms is explained in further detail in WO 01/89424.

$$z = \frac{\left(\frac{1}{R}\right)*r^2}{1+\sqrt{1-\left(\frac{1}{R}\right)^2(cc+1)r^2}} + ADr^4 + AEr^6 \quad (2)$$

Where R is the radial coordinate of the lens, cc is the conic constant, and AD and AE are coefficients of the polynomial extension.

TABLE 1

| i | $Z_i(\rho, \theta)$ (normalized format) | form associated with normalized polynomial |
|---|---|---|
| 1 | 1 | Piston |
| 2 | $2\rho\cos\theta$ | Tilt x |
| 3 | $2\rho\sin\theta$ | Tilt y |
| 4 | $\sqrt{3}(2\rho^2 - 1)$ | Defocus |
| 5 | $\sqrt{6}(\rho^2 \sin 2\theta)$ | Astigmatism $1^{st}$ order (45°) |
| 6 | $\sqrt{6}(\rho^2 \cos 2\theta)$ | Astigmatism $1^{st}$ order (0°) |
| 7 | $\sqrt{8}(3\rho^3 - 2\rho)\sin\theta$ | Coma y |
| 8 | $\sqrt{8}(3\rho^3 - 2\rho)\cos\theta$ | Coma x |
| 9 | $\sqrt{8}(\rho^3 \sin 3\theta)$ | Trifoil 30° |
| 10 | $\sqrt{8}(\rho^3 \cos 3\theta)$ | Trifoil 0° |
| 11 | $\sqrt{5}(6\rho^4 - 6\rho^2 + 1)$ | spherical aberration |
| 12 | $\sqrt{10}(4\rho^4 - 3\rho^2)\cos 2\theta$ | Astigmatism $2^{nd}$ order (0°) |
| 13 | $\sqrt{10}(4\rho^4 - 3\rho^2)\sin 2\theta$ | Astigmatism $2^{nd}$ order (45°) |
| 14 | $\sqrt{10}(\rho^4 \cos 4\theta)$ | Tetrafoil 0° |
| 15 | $\sqrt{10}(\rho^4 \sin 4\theta)$ | Tetrafoil 22.5° |

The spherical aberration of the lens is influenced by the shape factor of the lens. The spherical aberration of a spherical refractive lens can be minimized by a convex-plano lens (Atchison D. A., "Optical Design of Intraocular lenses. I: On-axis Performance", Optometry and Vision Science, 66 (8), 492-506, (1989)). The spherical aberration of the whole eye could be measured using a wavefront sensor. If only the cornea is considered well-known topographical measurement methods could be used. Such topographical methods are disclosed in for example "Corneal wave aberration from videokeratography: accuracy and limitations of the procedure", Antonio Guirao and Pablo Artal, J. Opt. Soc. Am. Opt. Image Sci. Vis., June, 17(6), 955-965, (2000). A wavefront sensor is described in U.S. Pat. No. 5,777,719 (Williams et. al.).

In the present invention, the amount of correction of spherical aberration depends on the shape factor of the lens. It is also possible to use a diffractive pattern that is able to at least partially correct for spherical aberration as well as for chromatic aberration. This can be done by modifying the higher orders of the phase function of the diffractive profile (lower orders, or terms on $r^2$ (Equation 1), describe the paraxial properties of the lens).

Other types of monochromatic aberrations can also be corrected for by aspheric refractive surfaces. The shape of the surface becomes more complex the higher the order of the aberration that is corrected. To compensate for a general aberration with an aspherical surface, the lateral height could be described by the equation below, $$z = \sum_{i=1}^{n} z_i$$

$$z_i = (asi)x^j y^k$$

$$i = 1/2\lfloor(j+k)^2 + j + 3k\rfloor$$

though also other descriptions are possible.

Where asi are the coefficients of the polynomial.

It is highly desirable that ophthalmic lenses designed according to the present invention, together with the eye provides a polychromatic image quality, which when expressed as MTF(50) (Modulation Transfer Function at 50 cycles per millimeter) performs at least about 40% higher than an aspheric lens compensating for the same spherical aberration as the inventive lens but without compensating for the chromatic aberration. A high value of the polychromatic image quality indicates that the amount of chromatic aberration is small and also that the amount of monochromatic aberrations is small.

In the present invention polychromatic image quality i be weighted to reflect the eyes sensitivity to different wavelengths of light under different lighting conditions, different viewing conditions or for different populations (i.e. using photopic, scotopic or mesopic luminosity functions, luminosity functions that reflect different spectral content of the viewing scene or lights used to illuminate the viewing scene, luminosity functions for populations of different race, presence of ocular disease or color vision deficiencies). In this way the lens will be optimized for these specific situations or groups of people.

Polychromatic image quality can be defined as follows:

Polychromatic MTF—The MTF for each wavelength calculated or measured is weighted by a spectral merit function f(λ)

$$PMTF(\lambda) = f(\lambda) * MTF(\lambda)$$

or $$PMTF(\lambda) = \sum_{i=1}^{n} f(\lambda_i) * MTF(\lambda_i)$$

and the form of the lens is optimized by maximizing the PMTF for a specified wavelength range (for example wavelengths transmitted by the eye or wavelengths in the visible range)

or

The longitudinal chromatic aberration (LCA) (i.e. difference in the effective focal length between the design wavelength and $\lambda_i$) is weighted by the spectral merit function for each wavelength considered. The form of the lens is then optimized to minimize this weighted longitudinal chromatic aberration (wLCA).

$$wLCA = f(\lambda)(efl(\lambda_d) - efl(\lambda))$$

OR $$wLCA = \sum_{i=1}^{n} f(\lambda_i) * LCA(i)$$

The lens can correct for the spherical aberrations and the chromatic aberrations as defined in a model eye. Spherical aberration of the eye can run between zero and 1.5 diopters, while chromatic aberration typically runs up to 2.5 diopters ("Optics of the Human Eye" written by David A. Atchison and George Smith).

The diffractive lens element exemplified with the present invention are diffractive surface profiles consisting of a number of concentric rings. The distances between the rings are decreasing out from the center of the lens. The area between two rings is called a zone. The width of the first zone is a constant that defines the widths of all the other zones; see A L Cohen in Applied Optics 31(19)(1992). The widths of the zones define the diffractive power of the lens. The parameter will be optimized using a spectral merit function.

According to a first example, the lens will be a monofocal lens and thus the profile height when multiplied by the difference in refractive index between the design lens and surrounding medium is equal to an integer number of the design wavelength. 550 nm is used as the design wavelength, since this is the wavelength for which the retina has its maximum sensitivity under photopic conditions (peak of the photopic luminosity function). It is chosen in this example to optimize the performance of the lens for photopic lighting conditions. When the profile height when multiplied by the difference refractive index between the design lens and surrounding medium is equal to one design wavelength, the lens will have its maximum effect in its first order. In general terms, the design wavelength may also be considered a variable in the design of the diffractive/refractive lens and may also be considered when selecting a spectral merit function, while the profile height could be proportional to any integer number of the design wavelengths ($\lambda_d/\Delta n$) and the design wavelength chosen will depend upon which lighting and viewing conditions the lens is optimized for. For scotopic conditions the design wavelength would be near 510 nm, the peak of the scotopic luminosity function. Any wavelength could be used as the design wavelength. The lens would then be monofocal for light of this wavelength.

The aberration corrections could all be full corrections or partial corrections. Furthermore all the corrections could be based on the aberrations of one or more parts of the eye. The corrections could also be based on either an average value of a certain population or on the measured values of the individual patient or on a combination of an average value and individual measurements. The certain population can be a group of people in a specific age interval or for example a group of people having had an eye disease or a corneal surgery. For chromatic aberration the values are substantially the same for all humans, so it is possible to take an average value of all kinds of people and correct for this chromatic aberration in the lens. Of course it is possible to do the same for spherical aberration but in this case it would be preferred to choose a group of people or even measure the spherical aberration for every individual since the spherical aberration will differ more from eye to eye than chromatic aberration. There are different possibilities for the design of the lenses according to the invention. One possibility is to design each lens for each individual. Then the chromatic aberration, the spherical aberration, the luminosity function for a selected lighting condition and the refractive error of the eye of the patient are measured and a lens is designed from these values according to the above-described method. Another possibility is to use average values from selected categories of people to design lenses adapted to suit almost all the people belonging to this category. It would then be possible to design lenses having different powers but providing the same reduction of spherical and chromatic aberration to patients within these groups of people. The groups of people could for example be age groups or groups of people having had specific eye diseases or a group of people having had a corneal surgery. Furthermore it would be possible to provide a kit of lenses having an average value of chromatic aberration and a range of different values of spherical aberration for each power. This could be preferred since the chromatic aberration is about the same in most human eyes and corneas. Hereby it would be necessary to measure the refractive error and the spherical aberration of each individual eye (or cornea for the case you were designing and intraocular lens) and then choose one lens from this kit of lenses to comply with these measurements.

In the following section, three examples of intraocular lenses (IOL) are described, which are designed using spectral merit functions. The exemplified IOLs correct for spherical aberration and for chromatic aberration of the pseudophakic eye. The examples use an aspheric lens surface for correcting the spherical aberration and a diffractive surface profile for correcting the chromatic aberration. In the examples the lens shapes are optimized to correct spherical aberration and chromatic aberration using a spectral merit function. In the examples the spectral merit function chosen to optimize the design of the achromat is the photopic luminosity function of the aphakic eye. Alternatively, the scotopic luminosity function, mesopic luminosity function or any other appropriately chosen wavelength dependent merit function could be used in its place to optimize the lens design for other corresponding conditions. The aspheric lens surface corrects the spherical aberration of the ocular surfaces, as well as the spherical aberration induced by the diffractive lens profile. In example 2 below, the IOL material contains a chromophore (spectral filter). This chromophore has filtering properties similar to natural human lens and as a result at least partially filters out the lower wavelengths. This serves to aid in the optimization procedure. In example 4, the IOL material contains a UV blocker and a yellow dye filter. The configuration of the example IOLs is fully described below, based on an eye model taken from the literature (Navarro et al, "Accommodation dependent model of the human eye with aspherics." JOSA A, 2(8), 1273-1281, (1985)) and based on the data of a polysiloxane intraocular lens material. The optical evaluation is done by ray tracing using the OSLO optical design software (Lambda Research Corporation, Littleton, Mass., USA).

EXAMPLE 1

A new lens is optimized using the photopic luminosity function of the aphakic eye as the spectral sensitivity merit function.

Background Theory:

Both the cornea and the refractive intraocular lens (IOL) have a positive chromatic aberration, which means that the focal length increases with longer wavelength. When the eye model of Navarro (1985) is used, together with a 20 diopter silicone refractive intraocular lens instead of the natural lens, the chromatic aberration can be estimated by calculating the power of the eye model at different wavelengths. A graph similar to FIG. 1 will be the result. A diffractive profile has a negative chromatic aberration. The profile consists of a number of rings (zones). For a diffractive lens working in the 1$^{st}$ diffraction order, the power of lens can be defined by:

$$P = \frac{2*\lambda}{w^2}$$

Where P is the lens power, λ is the design wavelength (m) and w is the Half-width (radius) of the first zone of the diffractive profile. The chromatic aberration (CA) can be described as:

$$CA = -\frac{\partial P}{\partial \lambda} = -\frac{2}{w^2}$$

Figure 1:
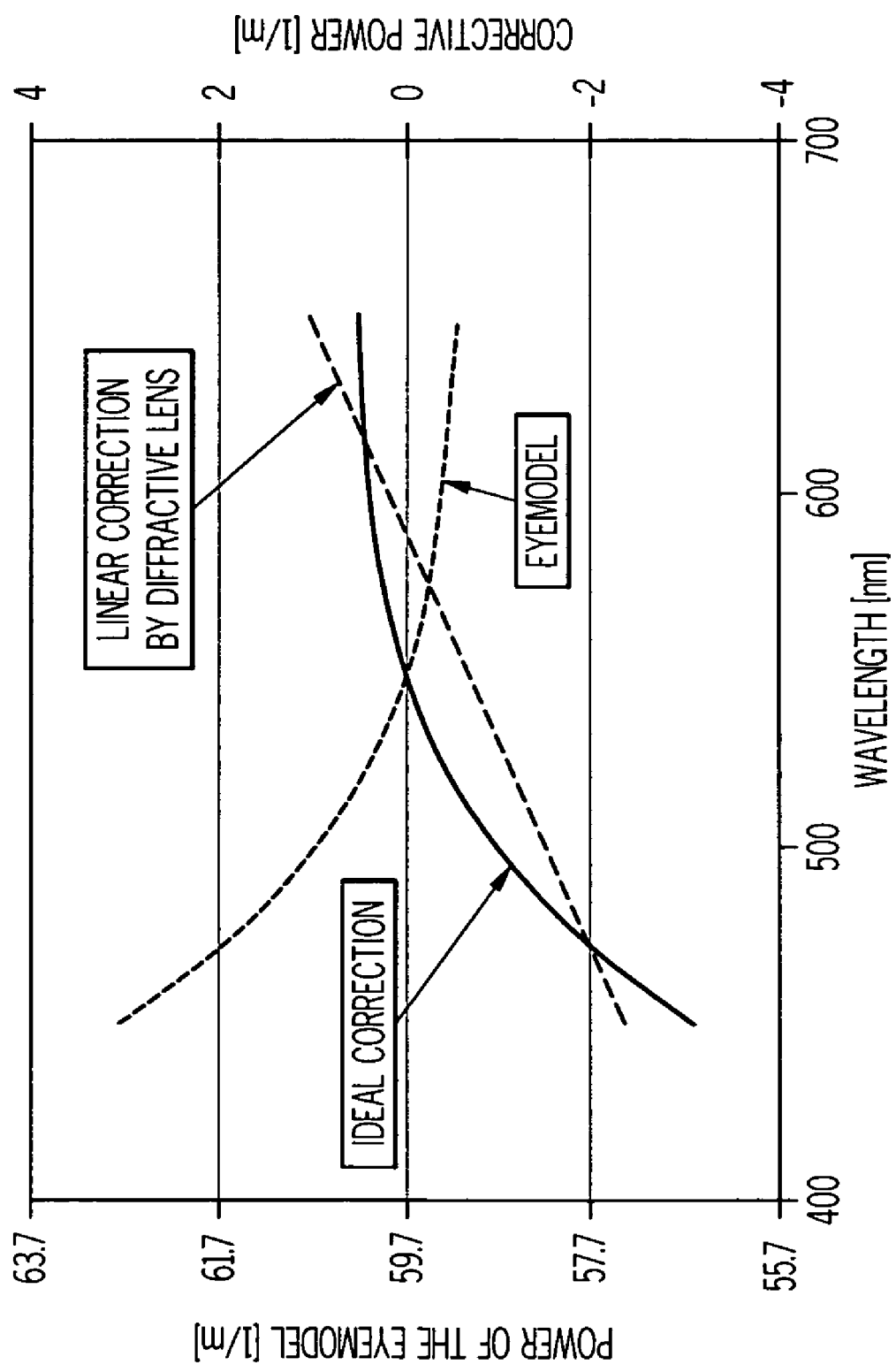
FIG. 1 shows a diagram of the relationship between refractive power and wavelength for an eye model and for a diffractive lens FIG. 2. shows the spectral merit function used to optimize the lens designed in Example 1. The pseudophakic spectral sensitivity function under photopic lighting conditions.

The diffractive lens power is linearly related to the wavelength. The relationship between refractive lens power and wavelength, in refractive systems, is generally not linear. This is also shown in FIG. 1. The eye model has a non-linear relationship and the diffractive lens has a linear relationship. A curve, representative for an ideal correction for the eye model is also shown. Therefore, a perfect correction cannot be made with a diffractive lens. Through the use of a spectral merit function (f(λ)), the characteristics of the diffractive profile can be optimized in order to minimize the effects of this non-perfect correction as will be illustrated in this example.

Figure 2:
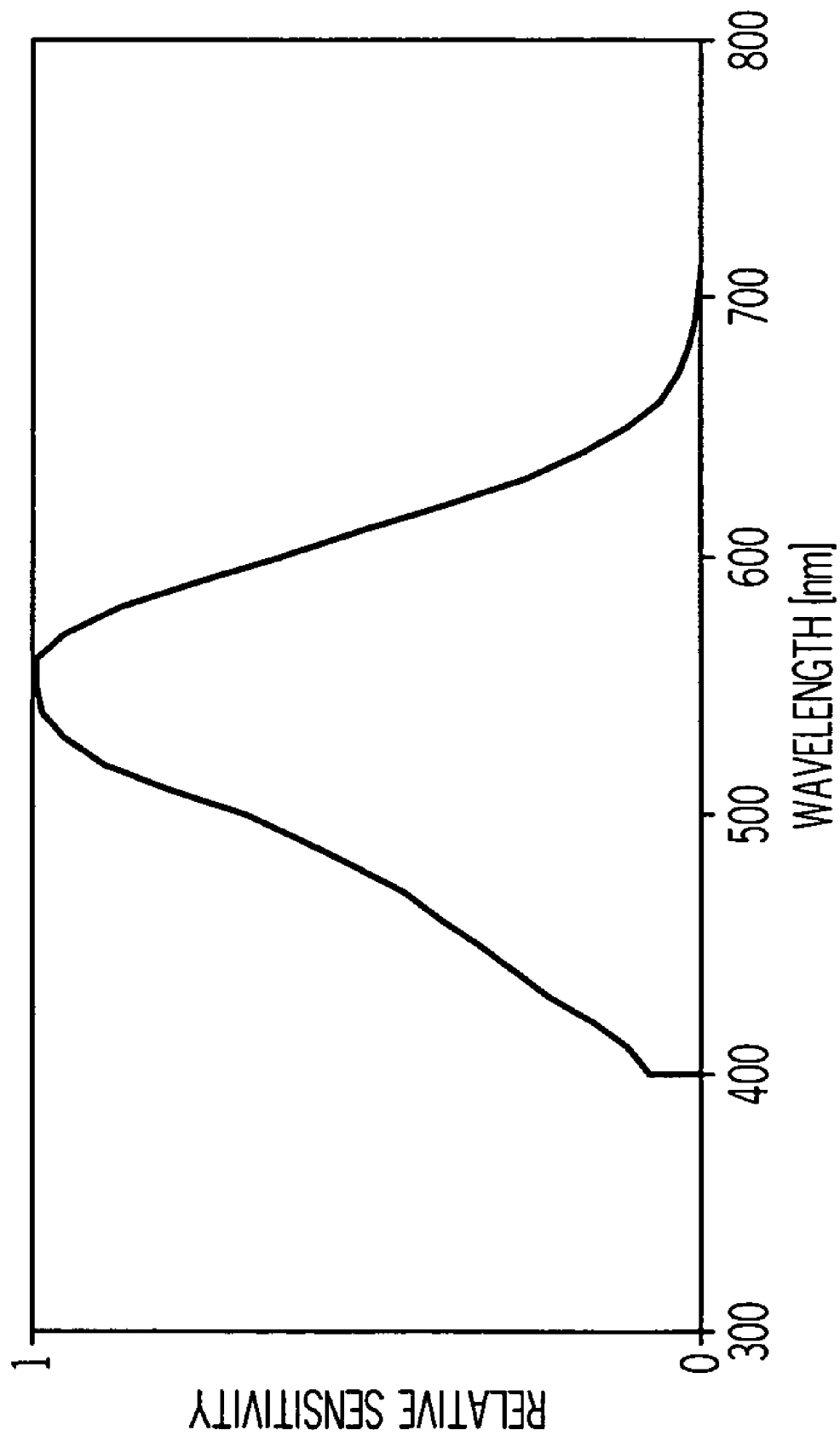

Description of the Lens:

The example lens is made of polysiloxane material. The material contains a regular UV-filter, which means that all light below a wavelength of 400 nanometers is blocked. These filters are commonly incorporated into intraocular lenses. The design wavelength chosen for this lens is 550 nm. Furthermore, the lens was optimized using a spectral merit function based on the pseudophakic photopic luminosity function. This pseudophakic photopic luminosity can be derived from the luminosity function of aphakic eyes and the UV filtering properties of the polysiloxane material. The aphakic luminosity function has been measured in a representative group of human subjects (Verriest, G. (1974). "The spectral curve of relative luminous efficiency in different age groups of aphakic eyes." *Mod Probl Ophthalmol* 13(0): 314-7 Griswold, M. S. and W. S. Stark (1992). "Scotopic spectral sensitivity of phakic and aphakic observers extending into the near ultraviolet." *Vision Res* 32(9): 1739-43)). The spectral merit function used in this example is shown in FIG. 2.

The shape of the lens used in this example is equi-biconvex. The anterior surface of the lens comprises an aspheric refractive surface, on which a diffractive profile is superimposed. The ratio of diffractive power to refractive power of this lens has been optimized using the spectral merit function in order to minimize the weighted chromatic aberration of the eye model and maximize the polychromatic modulation transfer function (also weighted) of the eye model. The diffractive profile has a lens power of 4.7 diopters, while the aspheric refractive lens has a lens power of 15.3D. The total resulting lens power is 20 diopters. The width of the first zone of the diffractive profile is 0.95 mm, and there are 38 rings needed to fill a full 6.0 mm IOL optic.

Eye dimensions, refractive indices and dispersion of the ocular media are used as described by Navarro (1985). This eye model includes an aspheric cornea. The surface information for the eye model and the lens is given in Table 2. The lens designed is dependent on the eye model chosen. It must be noted that it is possible to design lenses using other eye models or eye models constructed from actual physiological data from individual patients or groups of patients.

TABLE 2

| SRF | RADIUS | THICKNESS | APERTURE RADIUS | MEDIUM | NOTE |
|---|---|---|---|---|---|
| OBJ | — | 1.00E+20 | 1.00E+14 | AIR | |
| 1 | 7.72 | 0.55 | 2.55 | CORNEA | ASPHERE |
| 2 | 6.5 | 3.05 | 2.50 | AQUEOUS | |
| AST | — | — | 2.25 | AQUEOUS | |
| 4 | — | 0.9 | 2.25 | AQUEOUS | |
| 5 | 15.906 | 1 | 2.18 | SILICONE | ASPHERE, DIFFRACTIVE |
| 6 | −15.906 | 18.26 | 2.15 | VITREOUS | |
| IMS | −12 | 0 | 1 | — | RETINA |

| CONIC AND POLYNOMIAL ASPHERIC DATA | | | |
|---|---|---|---|
| Surface | conic constant | AD | AE |
| 1 | −0.260000 | — | — |
| 5 | 5.254 | −0.000672 | −6.28e−06 |

*DIFFRACTIVE SURFACE DATA (symmetric diffractive surface)

| Surface | Diffraction order | Design λ | Kinoform construction order | Kinoform zone depth | DF0 | DF1 |
|---|---|---|---|---|---|---|
| 5 | 1 | 0.550 μm | 1 | — | — | −0.00235 |

Behavior of the Lens:

The performance of the designed lens is evaluated in the eye model for 38 discrete wavelengths in the visible range between 390 to 760 nm (in 10 nm steps). The focus point is here defined as the point where the polychromatic MTF (Modulation Transfer Function) has it's maximum at 50 cycles/mm. The polychromatic MTF is determined by the weighted average of the MTF results at all wavelengths transmitted by the eye. The weighting of the wavelength dependent MTF was done using the luminance of the aphakic eye under photopic light conditions, which represents the relative sensitivity of the retina for different wavelengths. The calculations below are performed for a 4.5 mm aperture (pupil).

Figure 3:
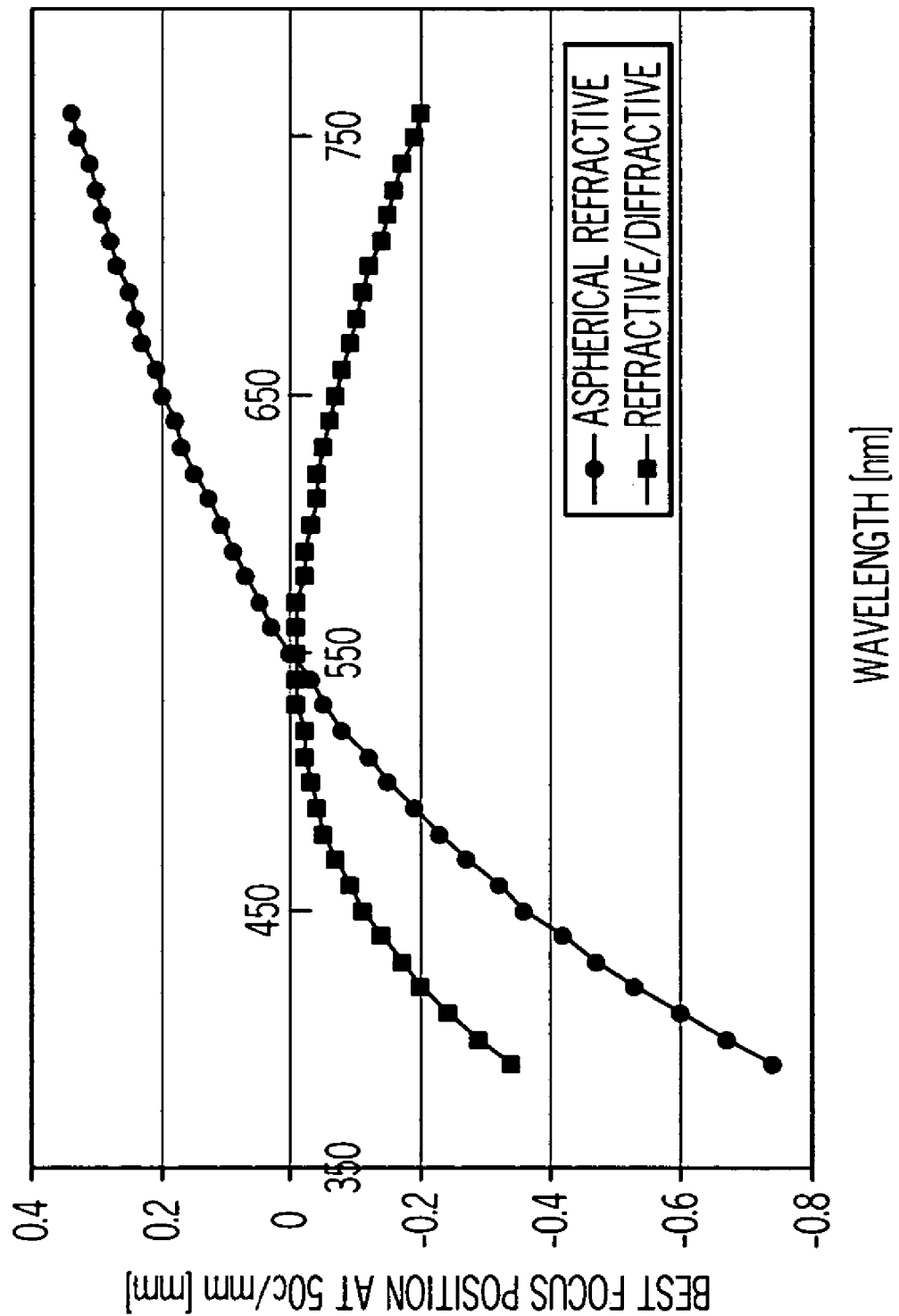
FIG. 3 shows the best focus position at 50 cycles per mm for a lens designed according to Example 1.

The actual back focal length (ABFL) values for the different wavelengths indicate the presence of a chromatic difference in focus and by definition the amount of longitudinal chromatic aberration. FIG. 3 shows the change in focal point versus the wavelength. The combined refractive/diffractive lens shows small amounts of variation in the focal point indicating low degrees of chromatic aberration. The wavelengths where the most deviation occurs are the wavelengths with low values of the spectral merit function indicating that these deviations occur for wavelengths that the eye is relatively insensitive to (wavelengths differing most from the design wavelength 550 nm).

Figure 4:
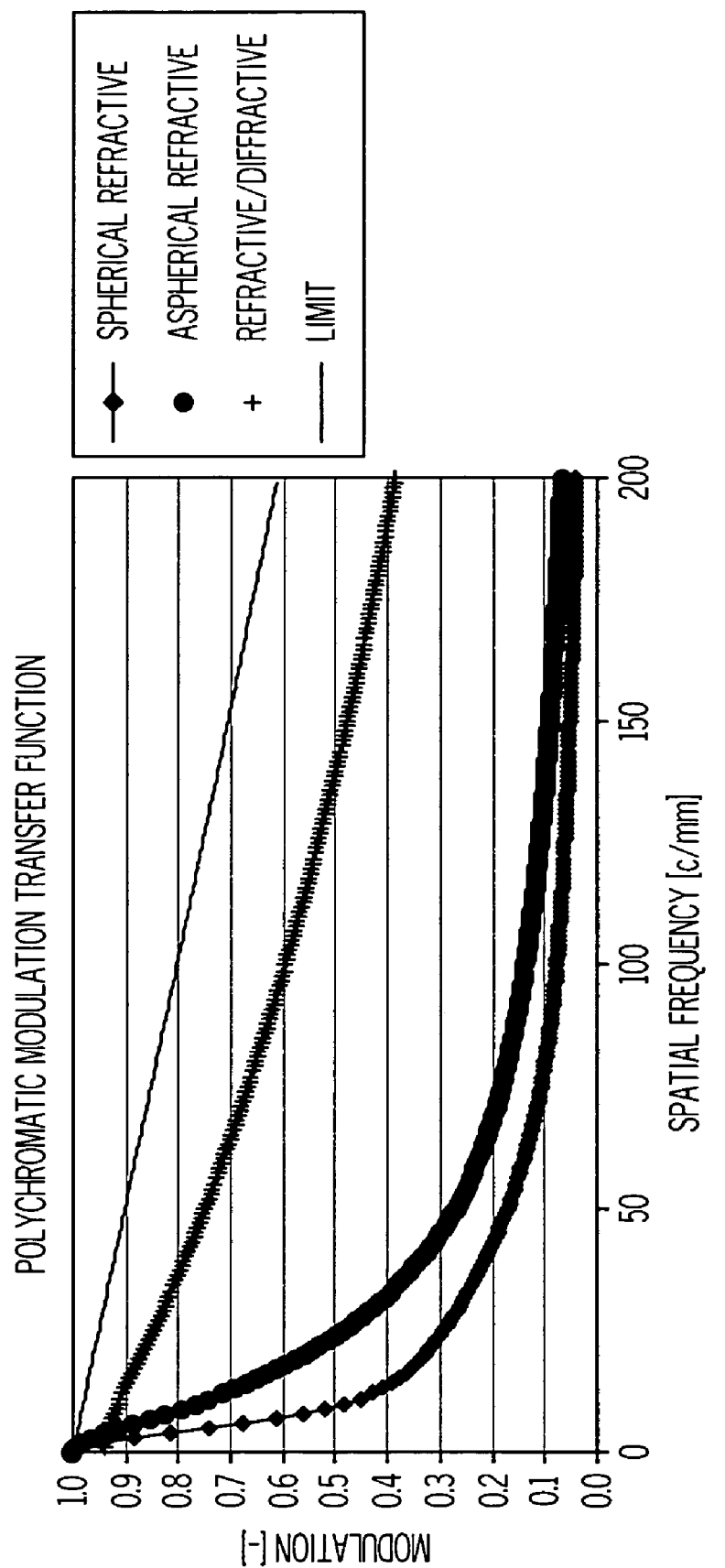
FIG. 4 shows polychromatic MTF curves for the refractive/diffractive lens designed in Example 1 shown compared to the polychromatic MTFs of a spherical refractive lens and an aspherical refractive lens.

Table 3 and FIG. 4 show the modulations at 50 cycles per millimeter for a spherical refractive lens, an aspherical refractive lens and a combined refractive/diffractive lens. Note that the refractive/diffractive lens also has an aspheric anterior surface. The table shows that the two aspheric lenses correct for spherical aberration, resulting in diffraction limited performance under monochromatic conditions. For the refractive/diffractive lens, the polychromatic performance is also nearing diffraction limited.

TABLE 3

| | monochromatic | | polychromatic | |
|---|---|---|---|---|
| | MTF50 | Limit | MTF50 | Limit |
| Spherical refractive | 0.29 | 0.90 | 0.17 | 0.90 |
| Aspherical refractive | 0.90 | 0.90 | 0.27 | 0.90 |
| Refractive/ diffractive | 0.90 | 0.90 | 0.75 | 0.90 |

EXAMPLE 2

A new lens is optimized using the photopic luminosity function of the aphakic eye as the spectral sensitivity merit function including a chromophore material This example illustrates the procedure followed when the refractive/diffractive lens material contains a chromophore (meaning the lens will have a wavelength dependent transmission function). In this example a refractive/diffractive intraocular lens design is again optimized using a spectral merit function to weight the wavelength dependent MTF following a similar procedure as that outlined in Example 1. In this case the combination of the chromophore and the diffractive portion of the lens optimized using a spectral merit function better minimize chromatic aberration and maximize the polychromatic MTF. Because the material contains a spectral filter that may filter out certain wavelengths completely or partially the wavelengths affected will contribute less to the polychromatic MTF. For optimization purposes the spectral filter can be included in the eye model so that its effects are included in the polychromatic MTF before the spectral merit function is applied to the optimization procedure or equivalently the filter can be left out of the eye model and the transmission factors of the lens can be added to the other weighting function in the spectral merit function (as a function of wavelength).

Description of the Lens:

The example lens is made of polysiloxane material, containing a chromophore that is equivalent to the natural crystalline lens. The design wavelength chosen for this lens is 550 nm and its shape is equi-biconvex. The anterior surface of the lens comprises an aspheric refractive lens, on which a diffractive profile is superimposed. The power ratio of the refractive portion of the lens to the diffractive portion of the lens is optimized using the polychromatic MTF weighted by the spectral merit function. In this case the spectral merit function consists of both the transmission function of the natural human lens (as a function of wavelength) and the aphakic photopic luminosity function.

Because the spectral merit function has been adjusted to include the transmission function of the natural lens the optimum ratio of refractive to diffractive power is different from that in Example 1. In this case the diffractive profile has a lens power of 4.5 diopters, while the aspheric refractive lens has a lens power of 15.5D. The total resulting lens power is again 20 diopters. The width of the first zone of the diffractive profile is 1.0 mm, and there are 36 rings needed to fill a full 6.0 mm IOL optic. In the periphery of the lens, the diffractive rings are 40 microns apart from each other.

Eye dimensions, refractive indices and dispersion of the ocular media are used as described by Navarro (1985). This eye model includes an aspheric cornea. The surface information for the eye model and the lens is given Table 4. The lens designed is dependent on the eye model chosen. It must be noted that it is possible to design lenses using other eye models or eye models constructed from actual physiological data from individual patients or groups of patients.

weighting of the wavelengths was done using the spectral merit function—the standard luminance of the eye under photopic light conditions, which represents the relative sensitivity of the retina for different wavelengths (equivalent to the addition of the transmission function of the natural lens to the aphakic luminosity function under photopic lighting conditions). The calculations are performed for a 4.5 mm aperture (pupil).

Figure 5:
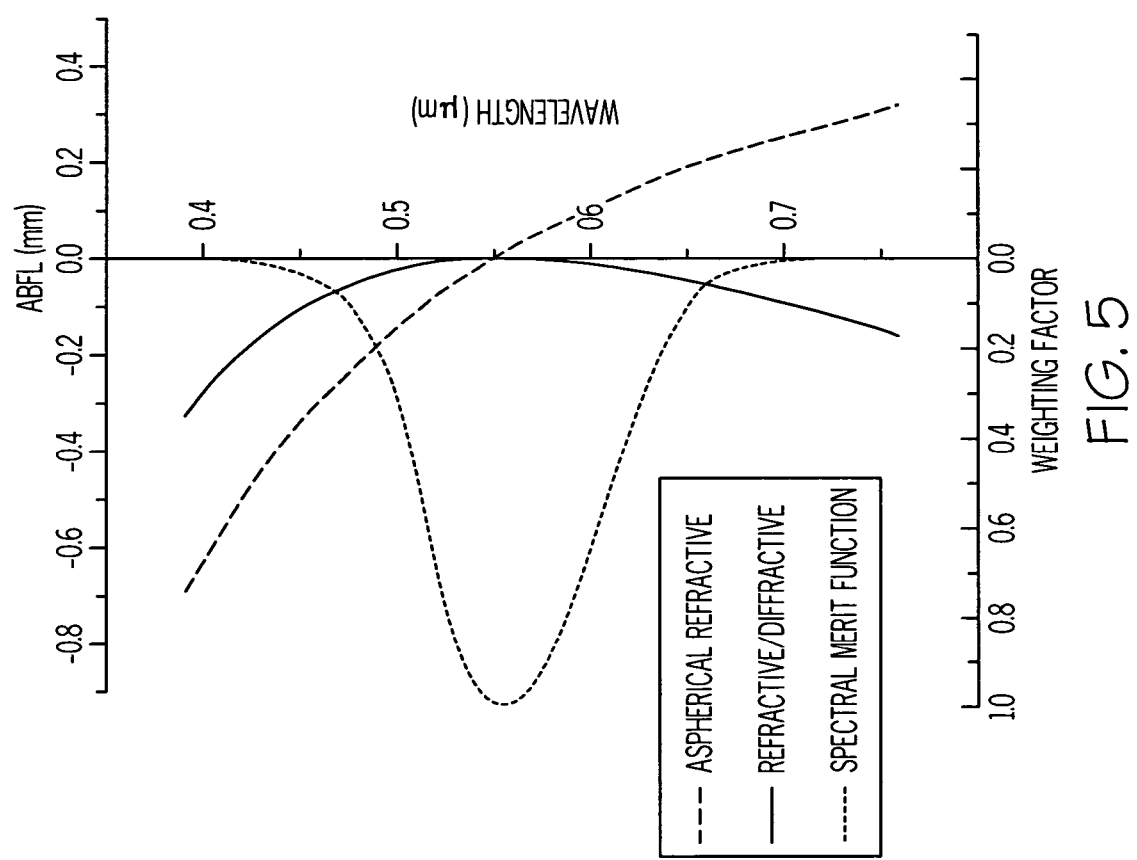
FIG. 5 shows the actual back focal lengths of the final lens design described in Example 2 overlain with the spectral merit function used to design this lens

FIG. 5 shows ABFL or the change in focal point versus the wavelength for the current example and an aspheric refractive lens. The spectral merit function used to design the lens is also included in FIG. 5. The combined refractive/diffractive lens shows less variation in the focal point indicating low degrees of chromatic aberration. The wavelengths where the most deviation occurs are the wavelengths with low values of the spectral merit function indicating that these deviations occur for wavelengths that the eye is relatively insensitive to (wavelengths differing most from the design wavelength 550 nm).

Figure 6:
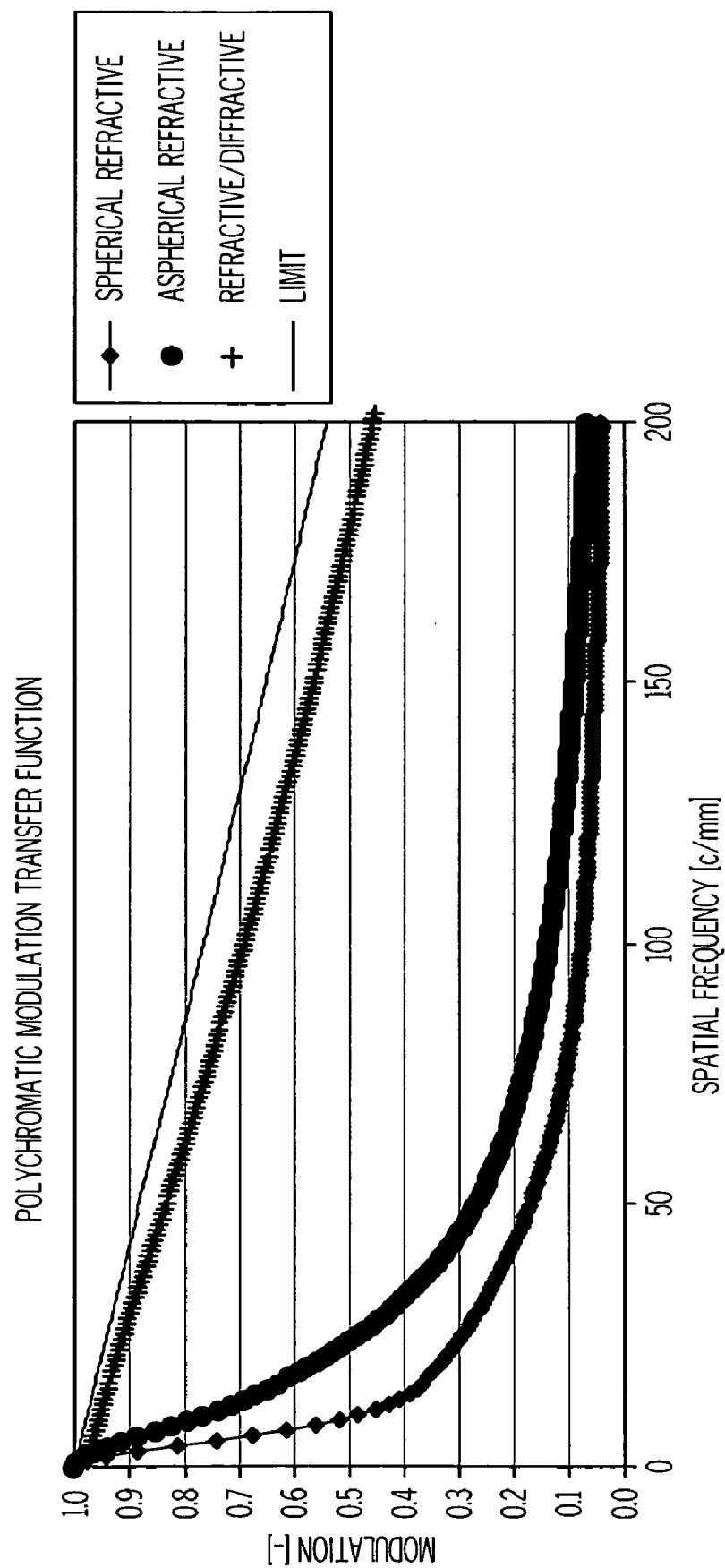
FIG. 6 shows polychromatic MTF curves for the refractive/diffractive lens designed in Example 2 shown compared to the polychromatic MTFs of a spherical refractive lens and an aspherical refractive lens.

Table 5 and FIG. 6 show the modulations at 50 cycles per millimeter for a spherical lens, an aspheric refractive lens and a combined refractive/diffractive lens. Note that the refractive/diffractive lens also has an aspheric anterior surface. The table shows that the two aspheric lenses correct for spherical aberration, resulting in diffraction limited performance under monochromatic lighting conditions. For the refractive/diffractive lens, the polychromatic performance is also approximately diffraction limited.

TABLE 4

| SRF | RADIUS | THICKNESS | APERTURE RADIUS | MEDIUM | NOTE |
|---|---|---|---|---|---|
| OBJ | — | 1.00E+20 | 1.00E+14 | AIR | |
| 1 | 7.72 | 0.55 | 2.55 | CORNEA | ASPHERE |
| 2 | 6.5 | 3.05 | 2.50 | AQUEOUS | |
| AST | — | — | 2.25 | AQUEOUS | |
| 4 | — | 0.9 | 2.25 | AQUEOUS | |
| 5 | 15.699 | 1 | 2.18 | SILICONE | ASPHERE, DIFFRACTIVE |
| 6 | −15.7 | 18.26 | 2.08 | VITREOUS | |
| IMS | −12 | 0 | 1 | — | RETINA |

| CONIC AND POLYNOMIAL ASPHERIC DATA | | | |
|---|---|---|---|
| Surface | conic constant | AD | AE |
| 1 | −0.260000 | — | — |
| 5 | −1.018066 | −0.000509 | −4.0423e−06 |

| *DIFFRACTIVE SURFACE DATA (symmetric diffractive surface) | | | | | | |
|---|---|---|---|---|---|---|
| Surface | Diffraction order | Design λ | Kinoform construction order | Kinoform zone depth | DF0 | DF1 |
| 5 | 1 | 0.550 μm | 1 | — | — | −0.002250 |

Behavior of the Lens:

38 discrete wavelengths over the visible spectrum of 390 to 760 nm (10 nm steps) were used to evaluate the eye model including the refractive/diffractive IOL. The focus point is here defined as the point where the polychromatic MTF (modulation transfer function) has it's maximum at 50 cycles/mm. The polychromatic MTF is determined by the weighted average of the MTF results at all wavelengths used. The

TABLE 5

| | monochromatic | | polychromatic | |
|---|---|---|---|---|
| | MTF50 | Limit | MTF50 | Limit |
| Spherical refractive | 0.39 | 0.88 | 0.17 | 0.88 |

TABLE 5-continued

|  | monochromatic | | polychromatic | |
|---|---|---|---|---|
|  | MTF50 | Limit | MTF50 | Limit |
| Aspherical refractive | 0.88 | 0.88 | 0.27 | 0.88 |
| Refractive/ diffractive | 0.88 | 0.88 | 0.84 | 0.88 |

EXAMPLE 3

Avoiding bifocal behavior of a diffractive lens element

Figure 7:
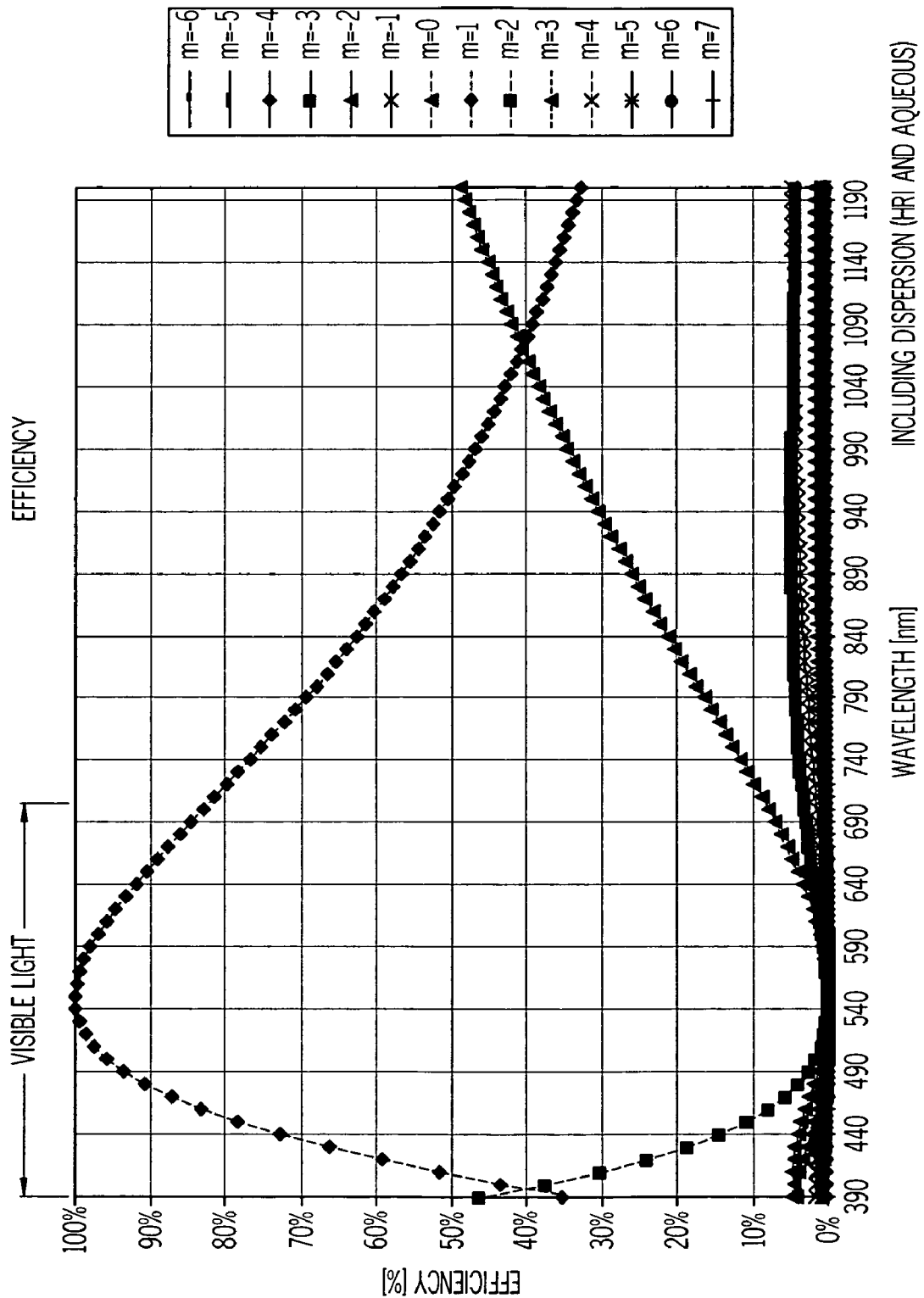
FIG. 7 shows the efficiency of different foci within a wavelength range 390 to 1190 nm for a lens with a design wavelength of 550 nm.

For a design lens of Example 1 (monofocal), the diffractive lens element has an efficiency, which depends on the wavelength of the light. At the design wavelength, the efficiency of the lens is 100%, which means that 100% of the light is directed to the intended focus point. At other wavelengths, the efficiency of the $1^{st}$ order focus decreases, while the efficiency of foci of the other diffractive orders increase. In FIG. 7, the change in efficiency for the different diffractive orders is depicted. The graph shows that for certain wavelengths, the lens becomes bifocal.

In FIG. 7, the diffractive lens has a design wavelength of 550 nm. This lens is bifocal at wavelength of 397 nm and 1070 nm. Only the lower wavelength (397 nm) lies within the range of visible light.

Figure 8:
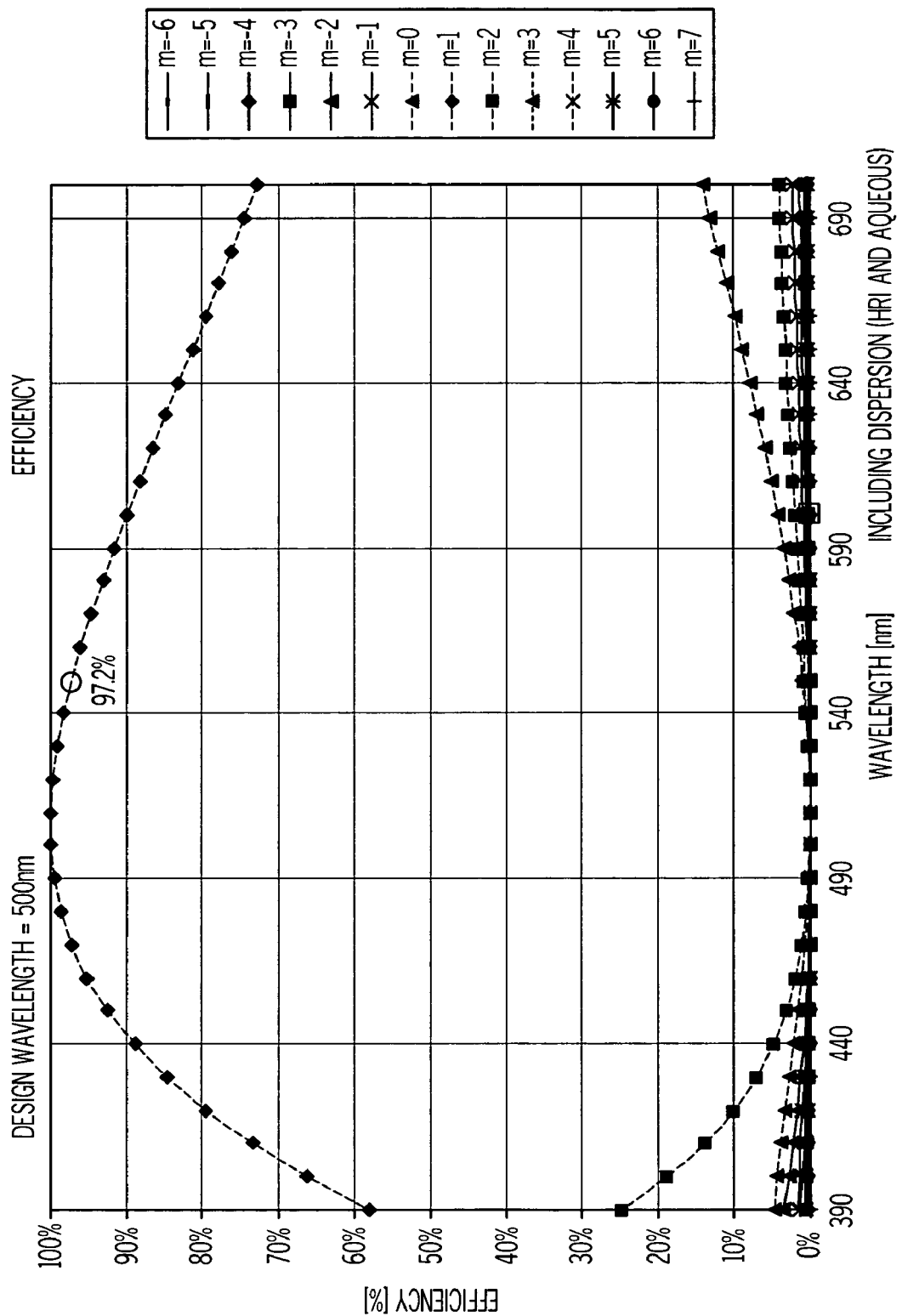
FIG. 8 shows the change in efficiency when the design wavelength is changed to 500 nm.

There are two ways to avoid a bifocal behavior in the visible light range:

1. Block the light at the specific wavelengths. For example, in this case light of wavelengths below ±420 nm should be blocked, at least partially, by a spectral filter.
2. Change the design wavelength of the diffractive lens. For example, lowering the design wavelength to 500 nm will shift the bifocal point to 369 nm, see FIG. 8 This wavelength is barely visible and will also be blocked by UV blockers regularly used in currently marketed IOLs.

EXAMPLE 4

A new lens, optimized for a lens material with an alternative spectral filter. In example 2, a lens material was used that had a specific transmission function as a function of wavelength, which was identical to that of the natural human eye. The spectral merit function combines the aphakic luminosity function with the transmission function of a natural crystalline lens. This combination is equivalent to the the standard (phakic) luminance of the eye. Here, an alternative spectral filter is used, specifically designed for use in an ophthalmic lens, with the purpose of, for example, protecting the retina for blue light, for improving the overall image quality, for avoiding the bifocality of a lens design, or for any other purpose.

Figure 9:
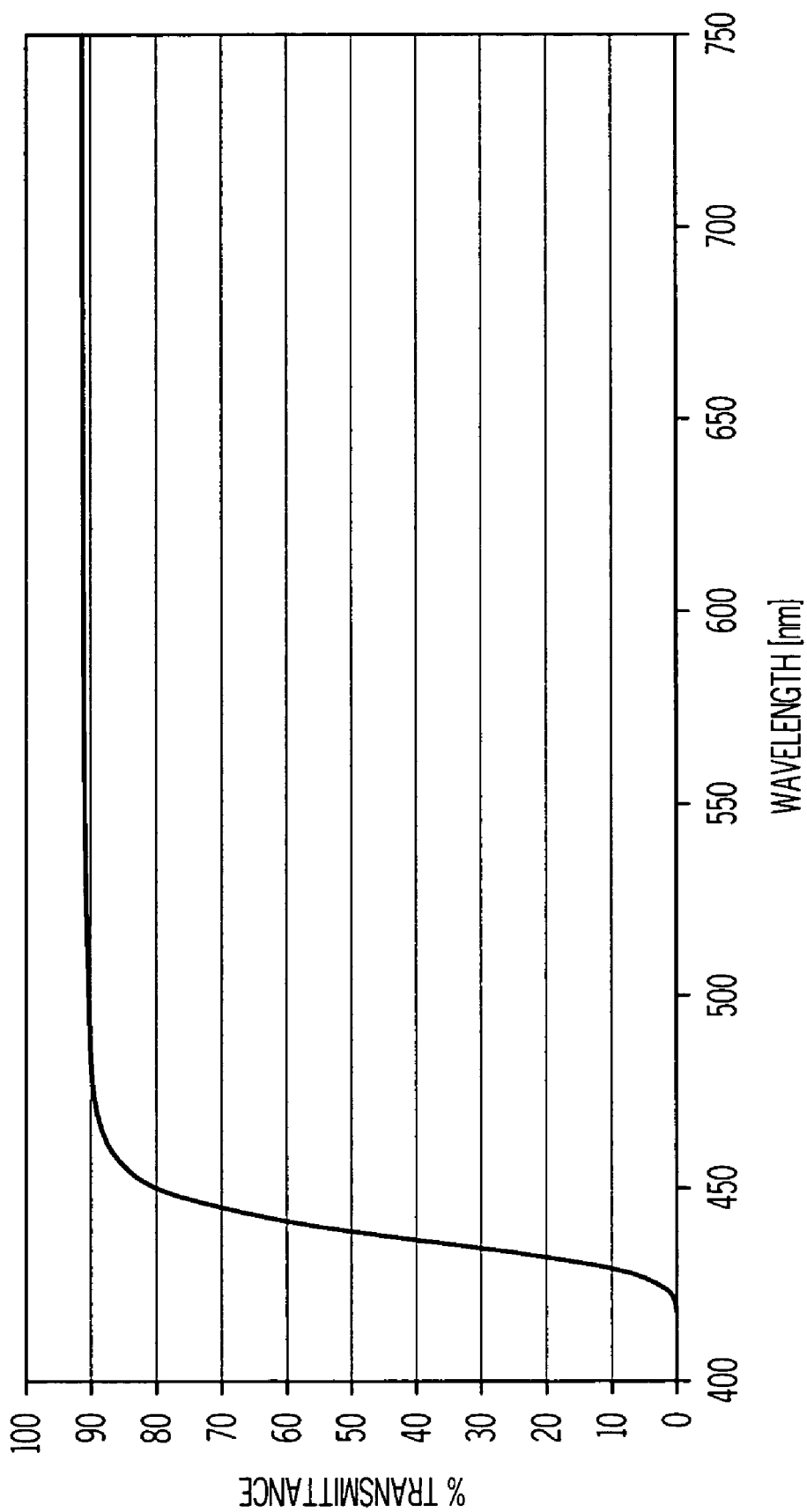
FIG. 9 shows the transmission curve of a lens having a UV blocker and a yellow dye filter.

Description of the Lens:

The lens in this example is similar to the lens in example 2, except for the transmission characteristics. The lens is made of polysiloxane or PMMA and contains a UV blocker as well as a yellow dye, an example of which is Eastman Yellow 035-MA1, in order to block UV and short wavelength blue light. The lens has a transmission curve as shown in FIG. 9. To obtain the spectral merit function, the lens transmission is combined with the aphakic photopic luminance of the eye. With the new spectral merit function, the lens is optimized using the same methods as in example 2. The optimized lens has a 4.7D diffractive lens power, while the total lens power is again 20 diopters.

Behavior of the Lens:

The optimized lens has a polychromatic MTF of 0.82 at 50 c/mm. As expected, this value is between the designs of example 1 and example 2; example 1 is without a filter and example 2 is with a relatively strong filter. The behavior follows a generate rule: the more light which is filtered out, the more the system behaves like a monochromatic system.

The invention claimed is:

1. A method of designing an aspheric ophthalmic lens with both refractive and diffractive powers that is capable of reducing chromatic aberration and at least one monochromatic aberration of an eye characterized by combining aspherical refractive and diffractive surfaces, selecting an appropriate eye model, establishing a design lens having at least one aspheric surface with a capacity to reduce monochromatic aberration in said eye model, establishing a diffractive lens element that corrects for chromatic aberration of the model eye; and adjusting the lens surface design in order to obtain a suitably high polychromatic image quality in a form that is weighted to comply with a spectral merit function, wherein said spectral merit function describes a wavelength dependent sensitivity of an eye for selected lighting conditions, wherein the spectral merit function is obtained from a combination of functions and wherein the functions are selected from the group consisting of photopic, scotopic, and mesotopic luminosity functions.

2. The method according to claim 1 including selecting a design wavelength deviating from the maximum sensitivity wavelength of the spectral merit function so the higher order foci generated from the diffractive lens element have sufficiently low efficiencies within the range of visible light.

3. The method according to claim 2, wherein the design wavelength is between 470 and 545 nm.

4. The method according claim 3, wherein the design wavelength is 500 nm.

5. The method according to claim 2, wherein the maximum sensitivity wavelength of the spectral merit function is 550 nm.

6. The method according to claim 1, wherein the design lens is provided with a wavelength filter that eliminates a wavelength range, or reduces transmission at selected wavelengths.

7. The method according claim 6, wherein the filter is a blue light chromophore.

8. The method according to claim 6, wherein the filter is equivalent to the natural crystalline lens at a specific age.

9. A method according to claim 1, wherein the lens is a monofocal lens.

10. The method of claim 1, wherein the design lens has an aspheric surface made to compensate for spherical aberration from a model cornea, wherein said model cornea is an average cornea resulting from averaged corneal topography determinations of an elected population, and wherein said population is elected to undergo cataract surgery.

11. The method according to claim 1, including evaluating if aberration terms signifying the aberrations of a wavefront have passing said design lens with a sufficiently chromatic aberration reducing diffractive element deviates from the preset capacity of the lens to correct for monochromatic aberration terms and optionally redesigning at least one surface of the design lens until the aberration terms sufficiently complies with said preset capacity.

12. The method according to claim 11, including evaluating aberration terms signifying spherical aberrations.

13. The method according to claim 11, wherein the surface redesign involves a change of the aspheric curve representing the lens surface.

14. The method according to claim 1, wherein said design lens is an intraocular lens.

15. A method of designing an aspheric ophthalmic lens with both refractive and diffractive powers that is capable of reducing chromatic aberration and at least one monochromatic aberration of an eye characterized by combining aspherical refractive and diffractive surfaces, selecting an appropriate eye model, establishing a design lens having at least one aspheric surface with a capacity to reduce monochromatic aberration in said eye model, establishing a diffractive lens element that corrects for chromatic aberration of the model eye; adjusting the lens surface design in order to obtain a suitably high polychromatic image quality in a form that is weighted to comply with a spectral merit function, wherein said spectral merit function describes a wavelength dependent sensitivity of an eye for selected lighting conditions, wherein the spectral merit function is obtained from a combination of functions, and wherein the function is selected from the group consisting of photopic, scotopic, and mesotopic luminosity functions; determining the efficiency for the higher order foci generated from the diffractive lens element, and introducing in said design lens a spectral filter that eliminates wavelengths or reduces transmission of wavelengths in a manner that said higher foci have reduced efficiency within the range of visible light.

16. The method according to claim 15, wherein the higher order focus is the second order focus and the spectral filter is a blue light filter.

17. The according to claim 16, wherein the blue light filter eliminates wavelengths below 420 nm.

18. A method of designing an aspheric ophthalmic lens with both refractive and diffractive powers that is capable of reducing chromatic aberration and at least one monochromatic aberration of an eye characterized by combining aspherical refractive and diffractive surfaces, selecting an appropriate eye model, establishing a design lens having at least one aspheric surface with a capacity to reduce monochromatic aberration in said eye model, establishing a diffractive lens element that corrects for chromatic aberration of the model eye; and adjusting the lens surface design in order to obtain a suitably high polychromatic image quality in a form that is weighted to comply with a spectral merit function, wherein said spectral merit function describes a wavelength dependent sensitivity of an eye for selected lighting conditions, wherein the diffractive lens element is a diffractive surface profile consisting of a number of concentric rings, and wherein the profile height of the diffractive surface profile, when multiplied with a difference in refractive index between the design lens and a surrounding medium equals an integer number of the design wavelength.

* * * * *